(12) United States Patent
Abdelghani

(10) Patent No.: US 7,420,095 B2
(45) Date of Patent: Sep. 2, 2008

(54) PURIFICATION PROCESS OF AROMATICS

(75) Inventor: Mohammed Sabri Abdelghani, Riyadh (SA)

(73) Assignee: Saudi Basic Industries Corporation, Riyadh (SA)

( * ) Notice: Subject to any disclaimer, the term of this patent is extended or adjusted under 35 U.S.C. 154(b) by 206 days.

(21) Appl. No.: 10/539,959

(22) PCT Filed: Dec. 19, 2002

(86) PCT No.: PCT/EP02/14568

§ 371 (c)(1),
(2), (4) Date: Apr. 24, 2006

(87) PCT Pub. No.: WO2004/056729

PCT Pub. Date: Jul. 8, 2004

(65) Prior Publication Data

US 2007/0004956 A1 Jan. 4, 2007

(51) Int. Cl.
*C07C 2/66* (2006.01)
*C07C 7/00* (2006.01)

(52) U.S. Cl. ............... 585/323; 585/319; 585/446; 585/467; 585/805; 208/257; 208/260

(58) Field of Classification Search ............... 208/257, 208/260; 585/323, 319, 446, 467, 804, 805
See application file for complete search history.

(56) References Cited

U.S. PATENT DOCUMENTS

| 2,232,761 | A | | 2/1941 | Balthis | |
| 2,778,863 | A | | 1/1957 | Maisel | |
| 3,485,884 | A | | 12/1969 | Davis | |
| 4,795,550 | A | * | 1/1989 | Sachtler et al. | 208/307 |
| 6,368,496 | B1 | * | 4/2002 | Brown et al. | 208/295 |
| 6,500,996 | B1 | * | 12/2002 | Brown et al. | 585/323 |
| 7,214,840 | B2 | * | 5/2007 | Lo et al. | 585/323 |

FOREIGN PATENT DOCUMENTS

GB    437023    10/1935

\* cited by examiner

*Primary Examiner*—Tam M Nguyen
(74) *Attorney, Agent, or Firm*—William J. Spatz

(57) ABSTRACT

Process for reduction of bromine index in aromatics, comprising the steps of feeding an aromatics feed stream which contains olefin impurities to a distillation column; withdrawing an overhead stream from the distillation column; subjecting at least a portion of the overhead stream to a treatment for the alkylation or polymerization of olefin in a clay treater to provide a purified overhead stream which is then injected to the aromatics feed stream.

15 Claims, 2 Drawing Sheets

PURIFICATION PROCESS OF AROMATICS

Figure 1:
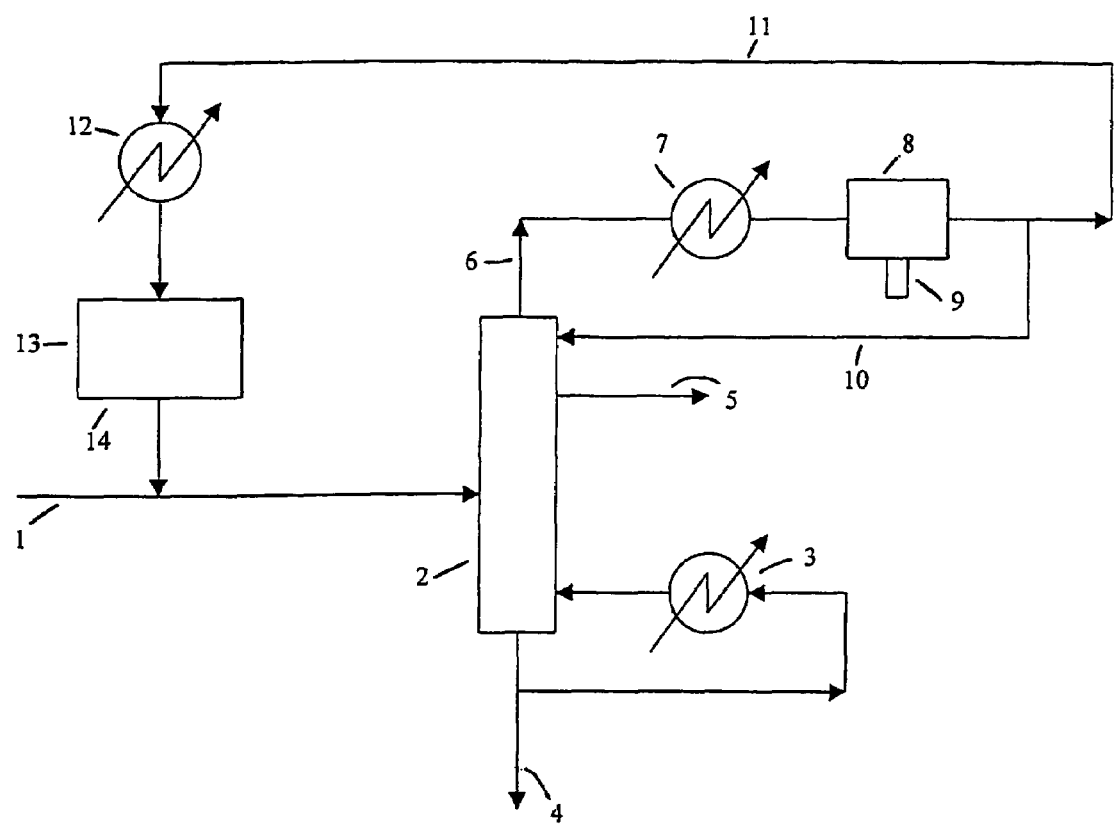

The present invention relates to a process for reduction of bromine index in aromatics production plants. Specifically, this invention relates to the arrangement of clay treaters used with distillation columns for the reduction of bromine index in BTX (benzene, toluene, xylene) production plants.

For use and further processing aromatics, such as benzene, toluene and xylene, have to be as pure as possible. One of the main issues regarding aromatics quality is the bromine index of aromatic products, which is defined as the number of milligrams of bromine that will react with trace olefins present in a 100 grams of an aromatics sample. The determination of the bromine index is an indication of the relative amount of olefins and diolefins, which are double-bounded straight-chain or cyclic hydrocarbons. Usually, a maximum bromine index of 10 is, e.g., required for benzene produced for a conversion into ethyl benzene. Generally, to reduce bromine index aromatics mixture is passed through clay or catalyst bed of alumina/silica in the liquid phase at high temperature and pressure, where a reaction occurs and the olefins are alkylated with a portion of the aromatic compounds forming heavier aromatics with more than 10 carbon atoms.

It is well known in the prior art that clay is used to alkylate or polymerize olefins in aromatic hydrocarbons followed by distillating in distillation columns to remove the polymers from column bottoms, as, for example, described in U.S. Pat. Nos. 2,778,863 and 3,485,884. The aromatic hydrocarbon mixture described can contain some or all of the following compounds: benzene, toluene, xylene, olefins and diolefins which could be produced from thermal cracking of naphtha and gas oil or from LPG cyclar process or any other process. It is known from the prior art that clay treater life will decline with time due to clay deactivation depending on the amount and type of olefins and diolefins in the feed and clay reaction temperature.

U.S. Pat. No. 6,315,964 discloses the production of linear alkyl benzenes (LAB) and points out that the presence of longer chain olefins compared to shorter chain olefins during clay alkylation reactions may lead to the formation of carbonaceous deposits and heavy organics in the clay bed. The presence and accumulation of water in the catalyst bed is also deleterious to catalyst activity which can form in-side reactions during alkylation or can be present in the inlet feed.

One of the main disadvantages in the prior art is that clay is exposed fully or partly to the aromatics feed with the various types of olefins chain length that can deactivate the catalyst bed quickly, especially if their concentrations are high. Also, the presence of high concentration of other impurities, such as heavy aromatics, nitrogen and sulfur compounds can lead to a much shorter clay life.

As a result, clay or catalyst bed upstream of distillation columns have an average service life of at best a few weeks depending on olefins and impurities concentrations and therefore have to be replaced frequently with fresh clay when bromine index in the distillate aromatic stream product exceeds the allowed level. This frequent replacement imposes financial as well as environmental burden on the process. Additionally, it demands extra labor time resources, which could be put in more useful use elsewhere in the production plant.

It is therefore an object of the present invention to overcome the disadvantages of the prior art, especially to provide a process for reduction of bromine index maintaining longer clay life while also maintaining low bromine index in the aromatic distillate product, such as benzene.

The object of the present invention is achieved by a process for reduction of bromine index in aromatics, comprising the steps of:
(I) feeding an aromatics feed stream to a distillation column;
(II) subjecting the aromatics feed stream to a distillation process;
(III) withdrawing an overhead stream and/or a product stream from the column;
(IV) subjecting at least a part of the overhead stream and/or the product stream to a treatment in a clay treater; and
(V) re-injecting an outlet stream of the clay treater to the aromatics feed stream.

Preferably the aromatics feed stream is fed to the distillation column at a tray about half way up the distillation column.

Particularly preferred is that the withdrawn overhead stream is collected in a receiver and any free water is collected in a water boot in the receiver.

In one embodiment one part of the withdrawn overhead stream is sent back to the distillation column as reflux.

It is preferred that another drag part of the withdrawn overhead stream is removed from the receiver and passed over the clay treater.

More preferred is that a smaller part of the withdrawn overhead stream is passed over the clay treater as drag stream.

According to a further embodiment of the invention the withdrawn overhead stream is cooled and preferably condensed in a heat exchanger prior to being collected in the receiver.

Still preferred is a process, wherein the condensed drag stream is, prior to entering the clay treater, heated in a heat exchanger and pressurized.

Preferably the aromatics feed stream comprises benzene, toluene, xylene, heavy aromatics, olefins, diolefines and the like.

More preferred is that the aromatics feed stream is fed to the distillation column with a bromine index of about 300 to about 1000, preferably about 500 to about 700.

According to the invention benzene distillate is a product stream withdrawn as side cut at a tray higher than the aromatics feed stream location.

In one embodiment of the invention heat is supplied to the distillation column by a reboiler at the column bottom by heating up a bottom stream having left the distillation column and being of least partly re-introduced.

It is preferred that the bottom stream comprises toluene, xylene and heavier olefines and aromatics.

Still preferred is that the aromatics feed stream is fed to the distillation column at a temperature of about 50 to about 100° C. preferably of about 75 to about 90° C., and a pressure of about 1 to about 10 barg, preferably about 1 to about 5 barg.

According to a further embodiment the bottom stream leaves the column at a temperature of about 120 to about 170° C., preferably 130 to about 150° C., and the product stream leaves the column at a temperature of about 75 to about 100° C., preferably about 85° C. to about 95° C.

In a further process of the invention the withdrawn overhead stream comprises about 97% benzene and has a bromine index of about 250 to about 350, preferably about 300 to about 320.

Moreover a process is preferred, wherein the drag stream of the withdrawn overhead stream to be subjected in the clay treater is removed with a flow rate of about 0.01-0.10 preferably about 0.03-0.05 of reflux flow rate, the low rate being the ratio of the flow rate of the drag stream to the flow rate of the reflux stream.

Still preferred is a process, wherein the drag stream to be subjected in the clay treater is treated in the clay treater at a temperature of about 150 to about 200° C., preferably 170 to about 180° C., and a pressure of about 10 to about 20 barg, preferably about 14 to about 16 barg.

Further, the process of the invention may be characterized in that the product stream comprises more than 99.90 wt.-% benzene and has a bromine index of about 5 to about 15, preferably about 8 to about 10.

Moreover, it is preferred that a further clay treater is placed upstream the distillation column.

It is further preferred that during a change over procedure at the end of service life an active downstream clay treater is used in place of deactivated upstream clay treater.

Finally, it is preferred that the product stream is as processed as the overhead stream.

Surprisingly, it was found that by the process according to the present invention the bromine index of a product stream of the distillation columns in an aromatics production plant are lowered to the desired level, wherein at the same time the service life of the clay treater used within that process is drastically increased in comparison to the prior art processes. This is due to the fact that not the complete aromatics feed is passed through the clay heater, but only a smaller part of the withdrawn overhead stream of the column is subjected to the clay treater. The aromatics with low bromine index already treated in the clay treater is mixed with the aromatics feed stream, so that the bromine index of the side cut aromatics distillate product stream will decrease reaching the required level. Also, as the withdrawn overhead stream continuously removes accumulated olefins in the reflux stream, this will keep the bromine index of the aromatics product stable. At the same time, since the clay treater is exposed to a clean stream of only one aromatic product, such as benzene, with close boiling olefins, the clay will not be contaminated quickly in comparison with the prior art, where it is exposed to the main aromatic stream mixture of column feed. For example, in benzene distillation columns, benzene is usually produced as a side cut stream above the feed tray while toluene and higher boiling diolefins and olefins are withdrawn from the column bottom. Lighter olefins and close boiling olefins to benzene accumulate in the reflux stream at the top of the column and are traditionally removed from the system in a small drag stream. According to the present invention, it is proposed, to treat the reflux stream at the top of the column, which contains mainly benzene and close boiling olefins, which accumulate in the reflux giving high bromine index, in a clay treater. This is achieved by passing the reflux drag stream at a sufficient flow rate to the clay treater at its designed temperature and pressure. The outlet stream from the clay treater will contain a low bromine index with olefin-alkylated heavy aromatics, the concentration of which will depend on the bromine index in the reflux drag. The treated stream is then re-injected into the aromatics feed stream of the distillation column, so that the heavy aromatics may be removed from the column bottom.

A further advantage of the process of the present invention is the value added cost of recovering benzene reflux drag that is considered as waste or an off specification product which is sold at low market price. An additional feature of this invention is the high purity product obtained without having a polishing column downstream to remove polymerized product. For example placing a clay treater downstream of a distillation column to reduce a distillate stream of benzene with bromine index from 70 to 0 by treating close boiling olefins will lead to the formation of heavy alkylated aromatics of about 700 weight ppm of aromatics with more than 11 carbon atoms in the benzene final product which will require another polishing column to maintain product quality. Another feature of the process according to the invention is that the returned flow of the treated reflux drag stream to the column feed does not constitute an overburden of the column capacity due to its small flow rate.

Figure 2:
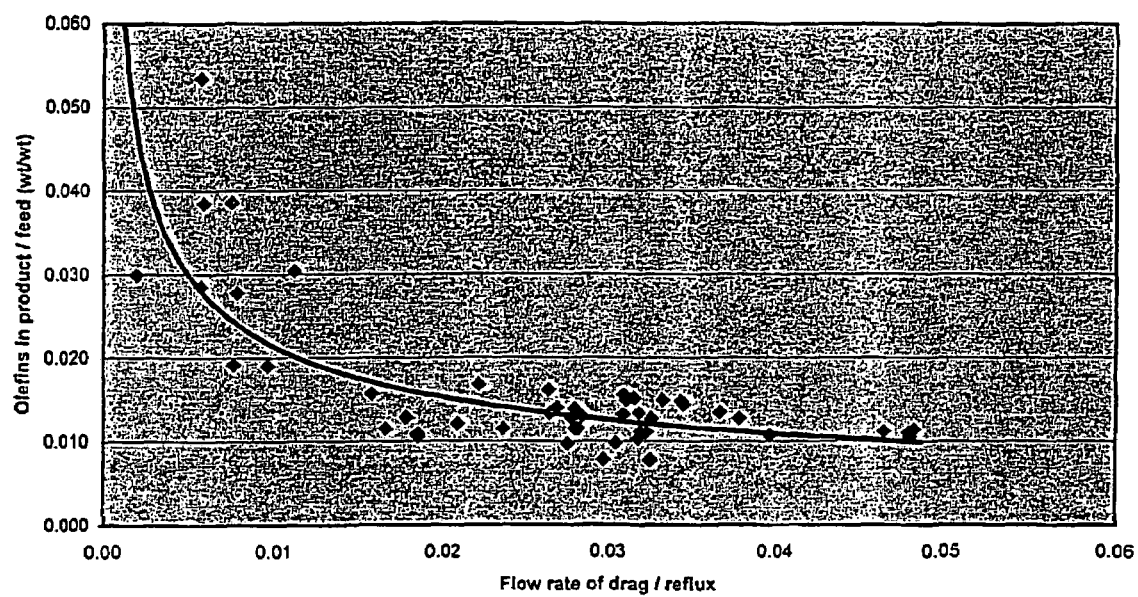

The invention is now being described more fully in the following detailed description and the following drawing, wherein FIG. 1 is a schematic representation of the process according to the present invention; and FIG. 2 is a graph showing the effect of drag on the bromine index of the aromatics product.

In the following, the process according to the present invention is explained in detail for a process using a distillation column to obtain benzene as the desired product. As apparent for someone skilled in the art, the process according to the present invention may be also utilized for other aromatics distillation columns, such as for toluene and xylene.

According to FIG. 1, an aromatics feed stream, comprising benzene, toluene, xylene and heavy aromatics together with accompanying olefins and diolefins, is fed via line 1 to a benzene distillation column 2 at a tray half way up the distillation column 2. Heat is supplied to the column 2 by a reboiler 3 at column bottom by heating up the bottom stream leaving the column via line 4 that comprises toluene, xylene and heavier olefins and aromatics, and re-introducing at least a part of the bottom stream into the column bottom. Benzene distillate is withdrawn as side cut via line 5 at a tray higher than the feed location. An overhead stream is withdrawn via line 6 from the column 2 and cooled in a heat exchanger 7, and the condensate is collected in a receiver 8. Any free water is collected in a water boot 9 in the receiver 8. The return flow is sent back to the column 2 as reflux via line 10. A part of the withdrawn overhead stream, a drag stream, is withdrawn from the receiver 8 and is passed to a heat exchanger 12 via line 1, where it is pressurized and heated to a temperature suitable for a clay treater 13. The drag stream is passed through the clay treater 13, the olefins are alkylated to heavier alkyl aromatics having more than 10 carbon atoms. The outlet stream of the clay treater 13 is fed back via line 14 to the column 2 and re-injected with the aromatics feed stream. Heavy alkylated aromatics may leave the column bottom in the bottom stream via line 4 with other heavy components, while treated pure benzene product stream leaves with the distillate stream via line 5 and lower bromine index due to a dilution effect.

Of course, the clay treater may further comprise silica-alumina. Additionally, the process of the invention may comprise a further clay treater upstream the distillation column, which arrangement is particularly suitable for a high bromine index of aromatics BTX stream, i.e. an index in excess of 600. During change over procedure at the end of service life in this arrangement, relatively active downstream clay treater can be used in place of the deactivated upstream clay treater. A fresh clay charge is then placed for the downstream clay treater.

Further, it is possible according to the invention that the overhead stream and/or the product stream, e.g. benzene, may be treated in the clay treater 13.

The invention is now further illustrated by way of experimental results. An aromatic feed stream of BTX comprising olefins with a bromine index of 560 is fed to a distillation column 2 at 82° C. and a pressure of 2 barg. The heavy aromatics stream leaves the column bottom at a temperature of 142° C. and the distillate product stream of benzene leaves the distillation column 2 at a temperature of 92° C. The overhead stream contains 97% benzene and the balance is saturated hydrocarbons and olefins with bromine index of 312 in the reflux. A small drag stream of the withdrawn overhead stream is removed from the system with a flow rate of about 0.03-0.05 of reflux flow rate. The drag stream is treated by feeding it into the clay treater 13 at a temperature of 175° C. and a pressure of about 15 barg. The outlet stream of the clay treater 13 is combined with the aromatics feed stream and is re-injected into the distillation column 2. The benzene product bromine index is in the range of about 8 to about 10 with purity of 99.94%, compared with a bromine index of 30-33 with benzene purity of 99.91% without applying the process of the present invention.

FIG. 2 shows the effect of increasing the drag stream flow rate in reflux stream against the olefin content in the product stream relative to that in the feed to the benzene column. It can be seen that for a constant amount of olefins content in the feed to the benzene column, the olefin content in the product stream decreases as the ratio of drag/reflux flow increases. A regression curve has been fitted to the data points to indicate the overall trend.

The features disclosed in the foregoing description, the claims and the drawings may, both separately and in any combination thereof be material for realizing the invention in diverse forms thereof.

The invention claimed is:

1. A process for for the purification of aromatics, comprising the steps of:
 (I) feeding an aromatics feed stream which contains olefin impurities to a multi-stage distillation column;
 (II) subjecting the aromatics feed stream to a distillation process in said distillation column;
 (III) withdrawing an overhead stream from the column;
 (IV) subjecting at least a portion of the overhead stream to a treatment for the alkylation or polymerization of olefins in a clay treater to provide a purified overhead stream; and
 (V) injecting the purified overhead stream from the clay treater into the aromatics feed stream.

2. The process according to claim 1, characterized in that the aromatics feed stream is fed to the distillation column at about a middle stage of the distillation column.

3. The process according to claim 2, characterized in that the withdrawn overhead stream is condensed and at least a portion of the condensed overhead stream returned to the distillation column as reflux.

4. The process according to claim 3, characterized in that a portion of the condensed overhead stream is heated and pressurized prior to treatment in the clay treater.

5. The process according to claim 3, characterized in that the aromatics feed stream has a bromine index of 300 to 1000.

6. The process according to claim 4, characterized in that the aromatics feed stream has bromine index is 500 to 700.

7. The process according to claim 3, characterized in that a benzene distillate product stream is withdrawn from the distillation column as side cut at a a distillation stage higher than the stage at which the aromatics feed stream is fed to the distillation column.

8. The process according to claim 7, characterized in that heat is supplied to the distillation column by by heating a bottom stream from the distillation column in a reboiler and re-introducing at least a portion of the heated bottom stream to a bottom stage of the distillation column.

9. The process according to claim 8, characterized in that the bottom stream comprises toluene, xylene and heavier olefins and aromatics.

10. The process according claim 7, characterized in that the aromatics feed stream is fed to the distillation column at a temperature of 75° C. to 90° C. and a pressure of 1 barg to 5 barg.

11. The process according to claim 8, characterized in that the aromatics feed stream is fed to the distillation column at a temperature of 75° C. to 90° C. and a pressure of 1 barg to 5 barg, the bottom stream leaves the distillation column at a temperature of 130° C. to 150° C., and the overhead stream leaves the distillation column at a temperature of 85° C. to 95° C.

12. The process according to claim 4, characterized in that the portion of the withdrawn overhead stream which is treated in the clay treater is 0.01-0.10 as large as the withdrawn overhead stream returned to the distillation column as reflux.

13. The process according to claim 12, characterized in that the portion of the withdrawn overhead stream which is treated in the clay treater is 0.03-0.05 as large as the withdrawn overhead stream returned to the distillation column as reflux.

14. The process according to claim 4, characterized in that the withdrawn overhead stream treated in the clay treater is at a temperature of 150° C. to 200° C. and a pressure of 10 barg to 20 barg.

15. The process according to claim 14, characterized in that the withdrawn overhead stream is treated in the clay treater at a temperature of 170° 0C. to 180° C. and a pressure of 14 barg to 16 barg.

\* \* \* \* \*